United States Patent [19]
Myers et al.

[11] Patent Number: 5,486,195
[45] Date of Patent: Jan. 23, 1996

[54] METHOD AND APPARATUS FOR ARTERIOTOMY CLOSURE

[76] Inventors: Gene Myers, 2727 S. Tamiami Trail, Suite 2A, Sarasota, Fla. 34239; William S. Coury, 2830 Bay Shore Cir., Sarasota, Fla. 34234

[21] Appl. No.: 97,401

[22] Filed: Jul. 26, 1993

[51] Int. Cl.$^6$ ............................................. A61B 17/04
[52] U.S. Cl. ........................ 606/213; 606/215; 606/191
[58] Field of Search ................................... 606/213, 214, 606/215, 230, 191–195; 604/15, 174, 96–102

[56] References Cited

U.S. PATENT DOCUMENTS

| | | | |
|---|---|---|---|
| 4,327,720 | 5/1982 | Bronson et al. | 604/174 |
| 5,104,377 | 4/1992 | Levine | 606/193 X |
| 5,108,421 | 4/1992 | Fowler . | |
| 5,163,906 | 11/1992 | Ahmadi | 606/194 |
| 5,171,222 | 12/1992 | Euteneur et al. | 606/194 X |
| 5,176,638 | 1/1993 | Michael | 606/194 X |
| 5,221,259 | 6/1993 | Weldon et al. | 606/213 X |
| 5,222,974 | 6/1993 | Kensey et al. | 606/213 |
| 5,275,616 | 1/1994 | Fowler | 606/213 |

OTHER PUBLICATIONS

M. Brennan, Blood Reviews, "Fibrin Glue", 5:240–244 (1991).

H. K. Kjaergard et al., Eur. J. Cardio-thorac. Surg., "Autologous Fibrin Glue Preparation and Clinical Use in Thoracic Surgery", 6:52–54 (1992).

Michael T. Stechison, J. Neurosurg., "Rapid Polymerizing Fibrin Glue From Autologous or Single–donor Blood: Preparation and Indications", 76:626–628 (1992).

Abbad G. Toma et al., The Journal of Laryngology and Otology, "Autologous Fibrin Glue in the Repair of Dural Defects in Craniofacial Resections", 106:356–357 (Apr. 1992).

R. A. Chisholm et al., Clinical Radiology, "Fibrin Sealant as a Plug for the Post Liver Biopsy Needle Track", 40:627–628 (1989).

Dennis F. Thompson et al., Drug Intelligence and Clinical Pharmacy, "Fibrin Glue: A Review of Its Preparation, Efficacy, and Adverse Effects as a Topical Hemostat", 22:946–952 (Dec. 1988).

Primary Examiner—Stephen C. Pellegrino
Assistant Examiner—Michael Peffley
Attorney, Agent, or Firm—Needle & Rosenberg

[57] ABSTRACT

The present invention provides an apparatus and a method for quickly and effectively sealing an arteriotomy site in a patient. In particular, the invention provides an apparatus and a method for sealing an arteriotomy site which can be performed by a single operator. The arteriotomy can be sealed by delivery of a patient specific autologous fibrin glue to a debrided, synthesized area adjacent to the extravascular opening of the arteriotomy.

20 Claims, 18 Drawing Sheets

METHOD AND APPARATUS FOR ARTERIOTOMY CLOSURE

BACKGROUND OF THE INVENTION

1. Field of the Invention

This invention relates to the sealing of a vascular puncture site. In particular, this invention relates to an apparatus for rapidly sealing an arterial puncture site using a naturally occurring sealant (e.g., a patient specific fibrin glue).

2. Background Art

Approximately 50 years ago, the Seldinger Technique of percutaneous entry into a vascular structure by use of a needle and a guidewire technique was introduced to modern medicine and subsequently has become the standard in the medical industry. Prior to Seldinger's discovery of entry into vascular structures, procedures required an incision through the skin and tissues, followed by an incision into the artery wall.

This earlier technique had numerous problems associated with it, i.e., infection, uncontrolled bleeding, trauma to the tissue and vessel wall. Thus, the advent of Seldinger's Technique was widely and rapidly accepted by the medical profession, and it became the world standard due to its advantages to both patient and doctor. The patient benefitted by less trauma, reduced risk of uncontrolled bleeding and vessel clotting, along with greatly reduced risk to infection. Doctors benefitted by the ease of entry and exit in the procedure.

Seldinger's Technique does not require suturing the artery puncture site or the skin and adjacent tissue as earlier procedures had required. Over the past 50 years, Seldinger's Technique has remained virtually unchanged, its many advantages far outweigh the main disadvantage—namely, the sealing of the arterial puncture site. Using Seldinger's Technique, in order to seal the arterial puncture site, it is necessary to apply strong pressure to compress the arterial wall sufficiently to reduce blood flow and intraluminal pressure to allow initiation of the body's own hemostatic processes. Typically, compression takes between 45 minutes to one hour before closure of the arteriotomy by natural clotting. Following this, inactivity with bed rest is required for eight to twelve hours to allow the clot to strengthen. The patient often cannot return to normal activity for up to two to three days following an arteriotomy procedure.

The medical, social, and economic impact of this prolonged recovery period is considerable. In fact, with over three million arteriotomy procedures annually in just the United States, the prolonged recovery period of the Seldinger technique has an economic impact of billions of dollars through an additional day's stay in hospital costs alone. Therefore, a need exists to develop a safe and effective means for sealing the arterial wall following arteriotomy procedures that allows the patient to quickly return to normal activity.

Additionally, other efforts have been attempted to solve the problem of sealing the arteriotomy site. For example, there is a current project underway using a foreign material (i.e., bovine collagen) to plug the arteriotomy site. These devices, however, rely on a non-removable biodegradable anchoring member to position the plug at the arteriotomy site. This anchoring member remains within the intraluminal space. The delayed biodegradation of the plug and its anchor can cause thrombus formation at the arteriotomy site.

Moreover, the FDA's current position on bovine collagen for use in plastic surgery (i.e., it hits been withdrawn pending further investigation) indicates an unlikeliness of these devices and foreign body plugs gaining medical and governmental acceptance. Therefore, there still exists a need for a safe and biocompatible agent and method for sealing an arteriotomy site.

SUMMARY OF THE INVENTION

The above disadvantages of the prior art are overcome by the present invention which provides an improved method and apparatus for arteriotomy closure. The apparatus comprises an elongated flexible catheter having a means for temporarily occluding the intravascular opening of the arteriotomy site and a means for delivering a material to the arteriotomy site that is capable of forming a substantially fluid tight seal of the arteriotomy site. The present invention may further comprise a means for debriding subcutaneous tissue from the exterior surface of the anterior arterial wall proximate to the arteriotomy site.

One embodiment the present invention provides an apparatus comprised of interlocking catheters with a tandem balloon design, wherein two balloons are arranged such that the first balloon functions to temporarily seal the intravascular opening of the arteriotomy, while the second balloon simultaneously debrides subcutaneous tissue from the external surface of the anterior arterial wall and creates an extra-vascular chamber in juxtaposition to the extravascular opening of the arteriotomy. The external chamber created by the second balloon is sufficient in size to receive from side ports in the first catheter a naturally occurring sealant (e.g., a patient specific fibrin glue) that rapidly and permanently closes the arterial puncture wound. The internal opening of the arteriotomy can remain temporarily occluded by the inflated intra-luminal balloon to prevent the liquid sealant material injected into the chamber from entering the bloodstream through the arteriotomy. As the sealant material is solidifying, the first catheter is withdrawn, and the second catheter is left in place to keep the sealant in proper position and to allow the solidifying sealant to seal the arteriotomy site.

In the past, it was necessary to compress the arterial wall with sufficient pressure to occlude the artery to stop bleeding at the arteriotomy site for approximately an hour to allow natural hemostatic processes to seal the puncture. Additionally, eight to twelve hours of supervised bed rest was required to complete the hemostasis. With the method and apparatus of the present invention, closure of the arteriotomy can be accomplished within 10–15 minutes with a single operator and there is no required period of bed rest following the procedure. The present invention thus greatly reduces the total time and labor required to complete the arteriotomy closure procedure.

The present invention also provides a means for sealing the arteriotomy site using a patient specific sealant, e.g., autologous (patient specific) fibrin glue. The usefulness of this glue has been documented in a wide range of medical applications. The fibrin glue may be manufactured from the patient's own blood. Using the patient's own blood drastically reduces the risk of transmitting disease (e.g., hepatitis or AIDS) which is always present when donor blood is used. The method for making patient specific fibrin glue is safe, inexpensive, and fast. The final product can be obtained within 30–60 minutes after collection of the blood.

DESCRIPTION OF THE PREFERRED EMBODIMENTS

Figure 1A:
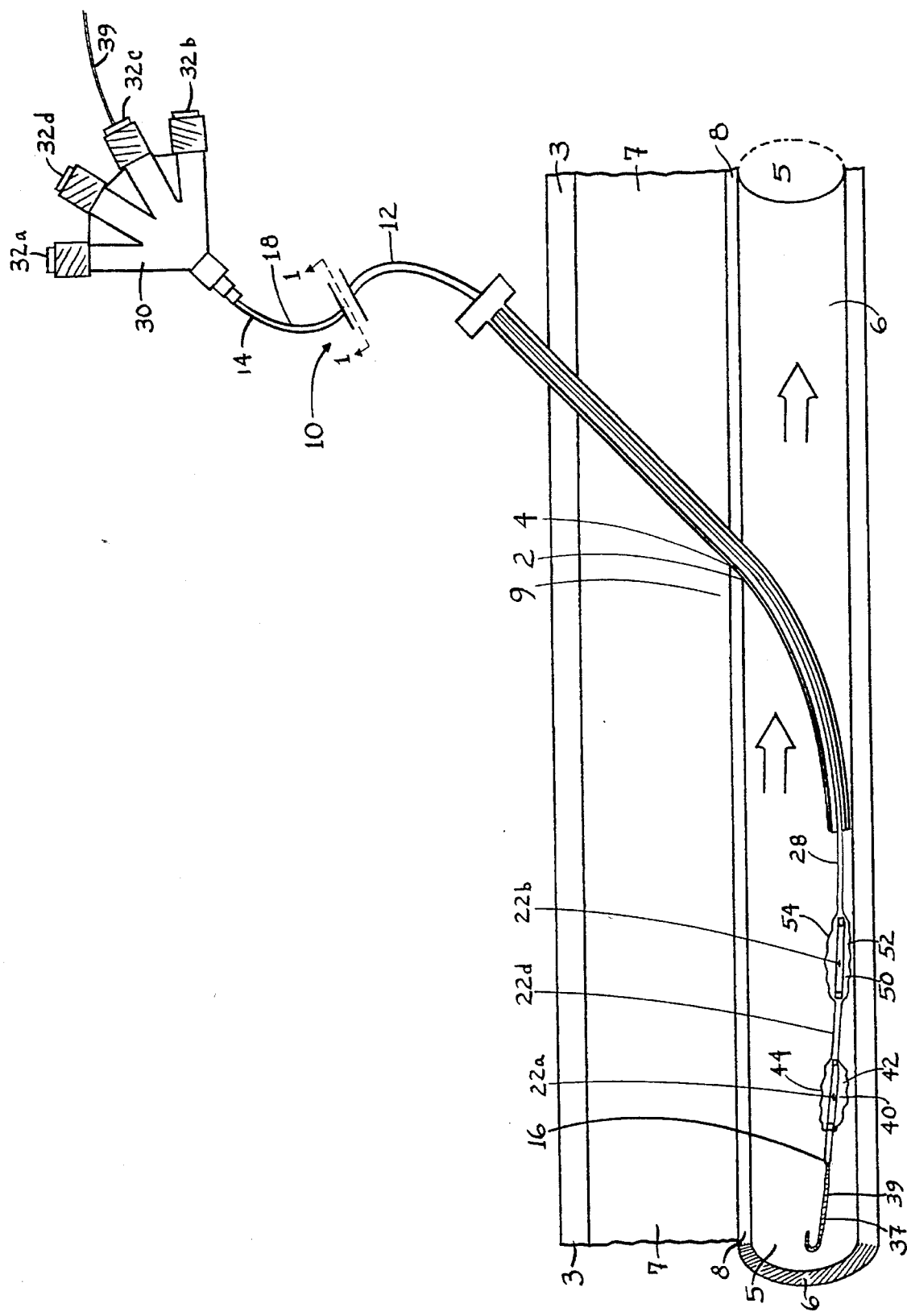
FIG. 1A is a longitudinal cross section of the arteriotomy site showing the relative location of the skin, subcutaneous tissue, the walls of the arterial structure, the arterial lumen, and the direction of blood flow. One embodiment of the apparatus of the present invention is inserted into the arterial lumen through the arteriotomy opening.

The present invention may be understood more readily by reference to the following detailed description of specific embodiments and the Examples and Figures included therein.

As used in the claims, "a" can mean one or more.

Referring now to FIGS. 1–4, one embodiment of the arteriotomy closure apparatus 10 is shown. The apparatus 10 for sealing the arteriotomy site 2 comprises a first elongated flexible catheter 12, a means 40 for temporarily occluding the intravascular opening 4 of the arteriotomy site 2, and a means for delivering a material to the arteriotomy site 2 that is capable of forming a substantially fluid tight seal of the arteriotomy site 2. The first flexible catheter 12 has a proximal end 14, a distal end 16, an external surface 18, a wall portion 28 defining at least one lumen 26a–d which extends substantially the entire length of the first catheter 12, and at least one opening 22a–d through the external surface 18 of the catheter 12 which is located adjacent to the distal end 16. The proximal end 14 of the lumen 26 is in fluid communication with the external surface 18 of the first catheter 12 via the opening 22.

The first catheter 12 may further comprise a collar 30 having at least one port 32. The port 32 is connected to the lumen (or lumens) 26 of the first catheter 12 at its proximal end 14 such that each port 32 of the collar 30 is in fluid communication with one of the lumens 26a–d of the first catheter 12.

The means 40 for temporarily occluding the intravascular opening 4 of the arteriotomy site 2 can be located adjacent to the distal end 16 of the first catheter 12. During arteriotomy closure, the occluding means 40 is positioned in the intravascular space of the patient's artery 6 proximate to the arteriotomy site 2. The occluding means 40 may comprise an intravascular expandable member 42 on the external surface 18 of the first catheter 12. The intravascular expandable member 42 can be a first balloon 44, which is a closed volume, surrounding a portion of the external surface 18 of the first catheter 12. The first balloon 44 overlays a first opening 22a in the external surface 18 of the first catheter 12.

Figure 1B:
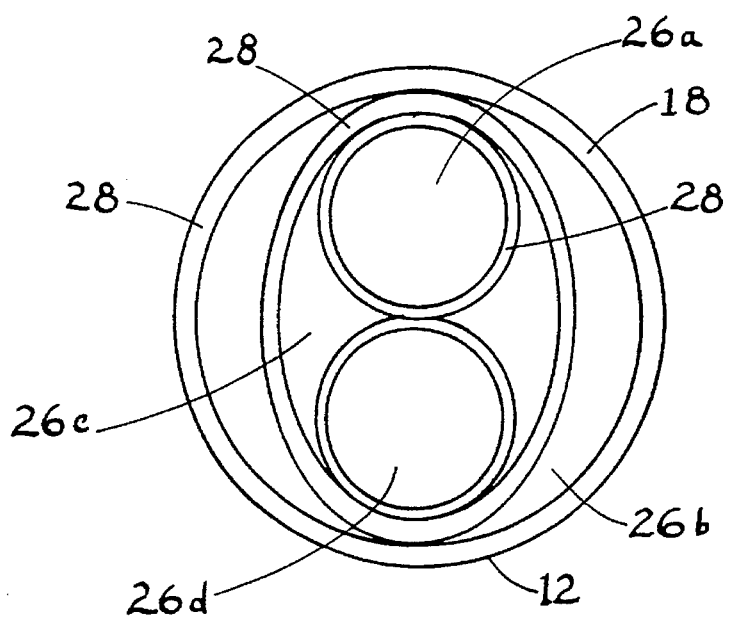
FIG 1B is a cross-sectional view of the catheter shown in FIG. 1A taken along lines 1—1.
Figure 1B:
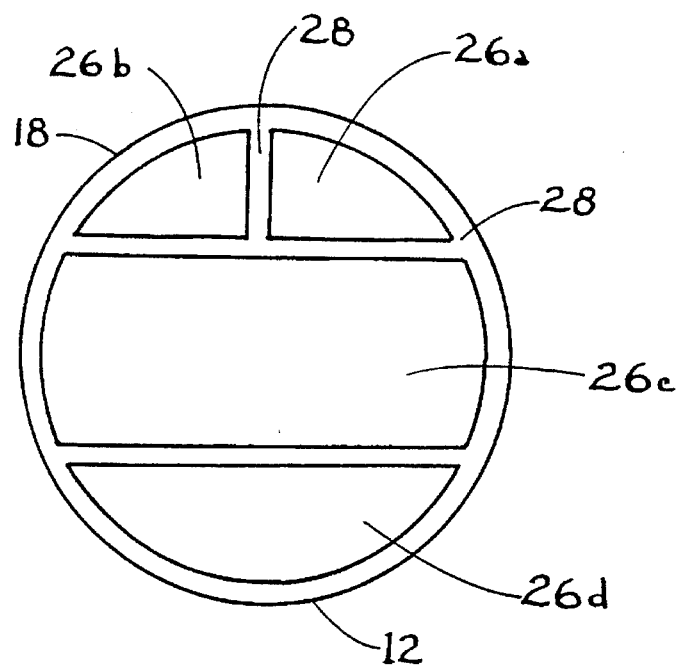
Figure 2:
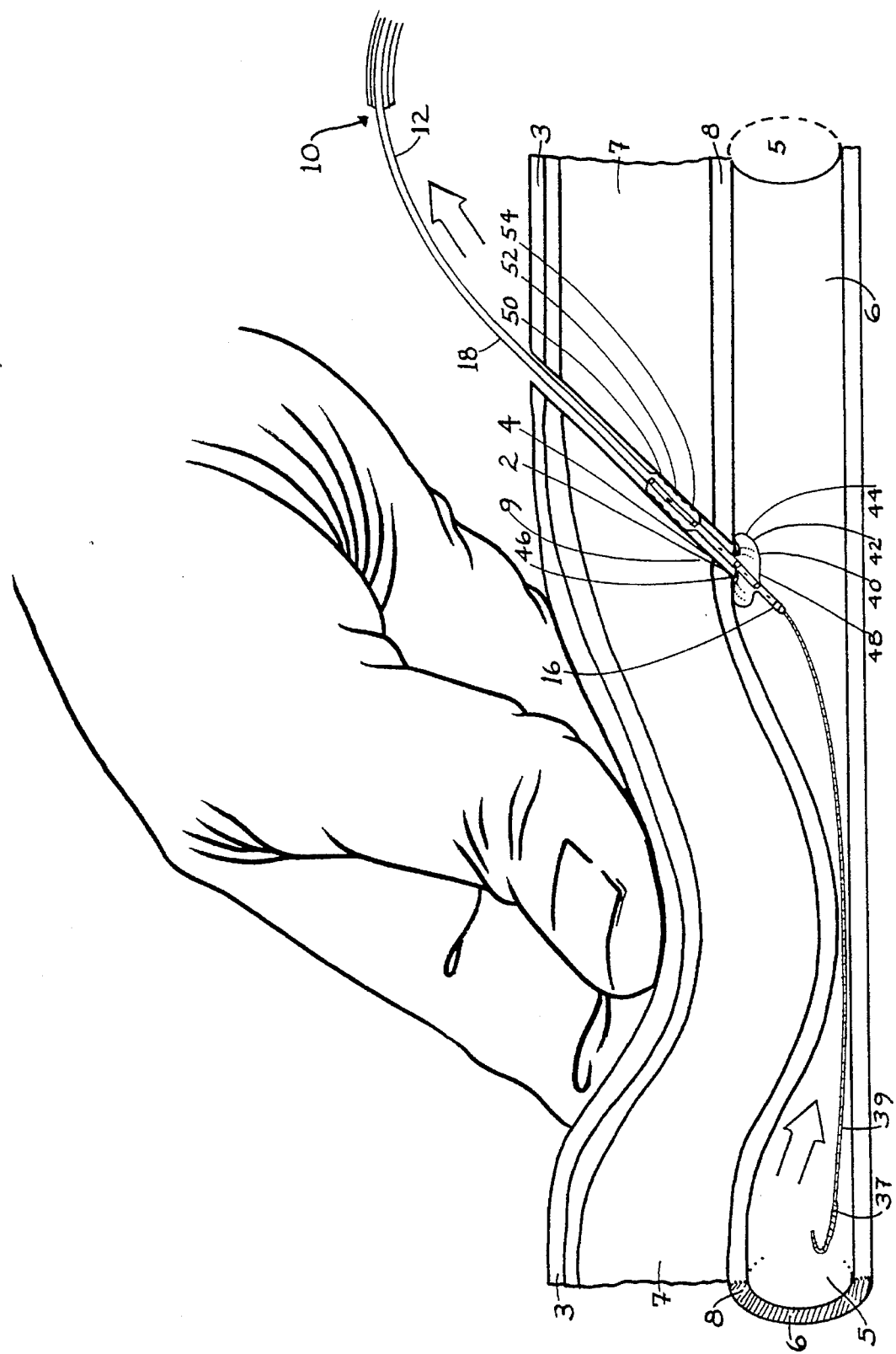
FIG. 2 shows external compression of the arterial lumen sufficient to impede blood flow and reduce intra-luminal pressure in order to prevent seepage of blood through the arteriotomy site during positioning of the apparatus shown in Fig. 1. The sheath is withdrawn to a position external to the skin, and the first balloon inflated and positioned so as to occlude the internal opening of the arteriotomy.
Figure 3:
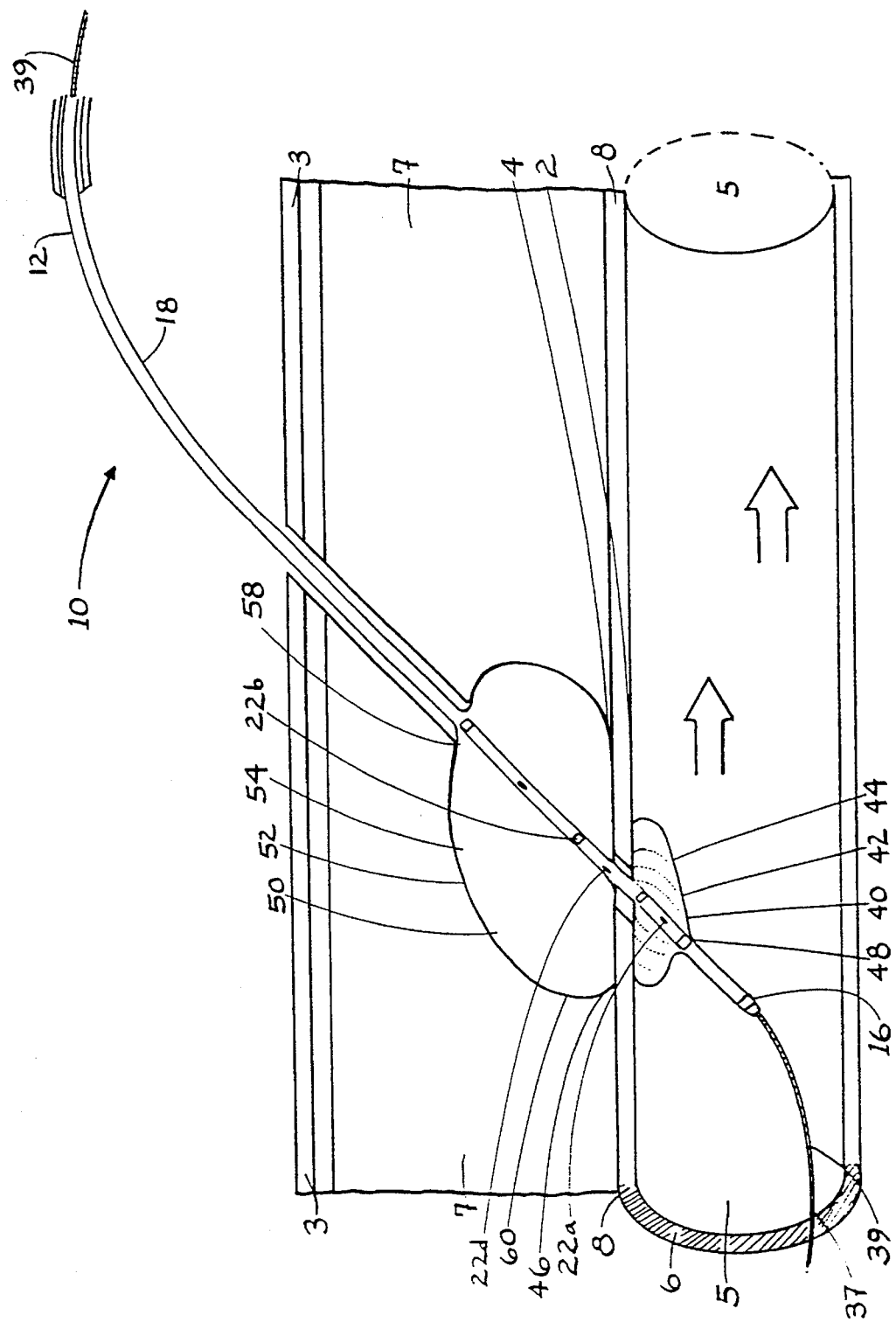
FIG. 3 depicts the apparatus shown in FIG. 1 and FIG. 2 with continued occlusion of the arteriotomy site by the first balloon while simultaneously inflating the second balloon to debride the anterior arterial wall.
Figure 4:
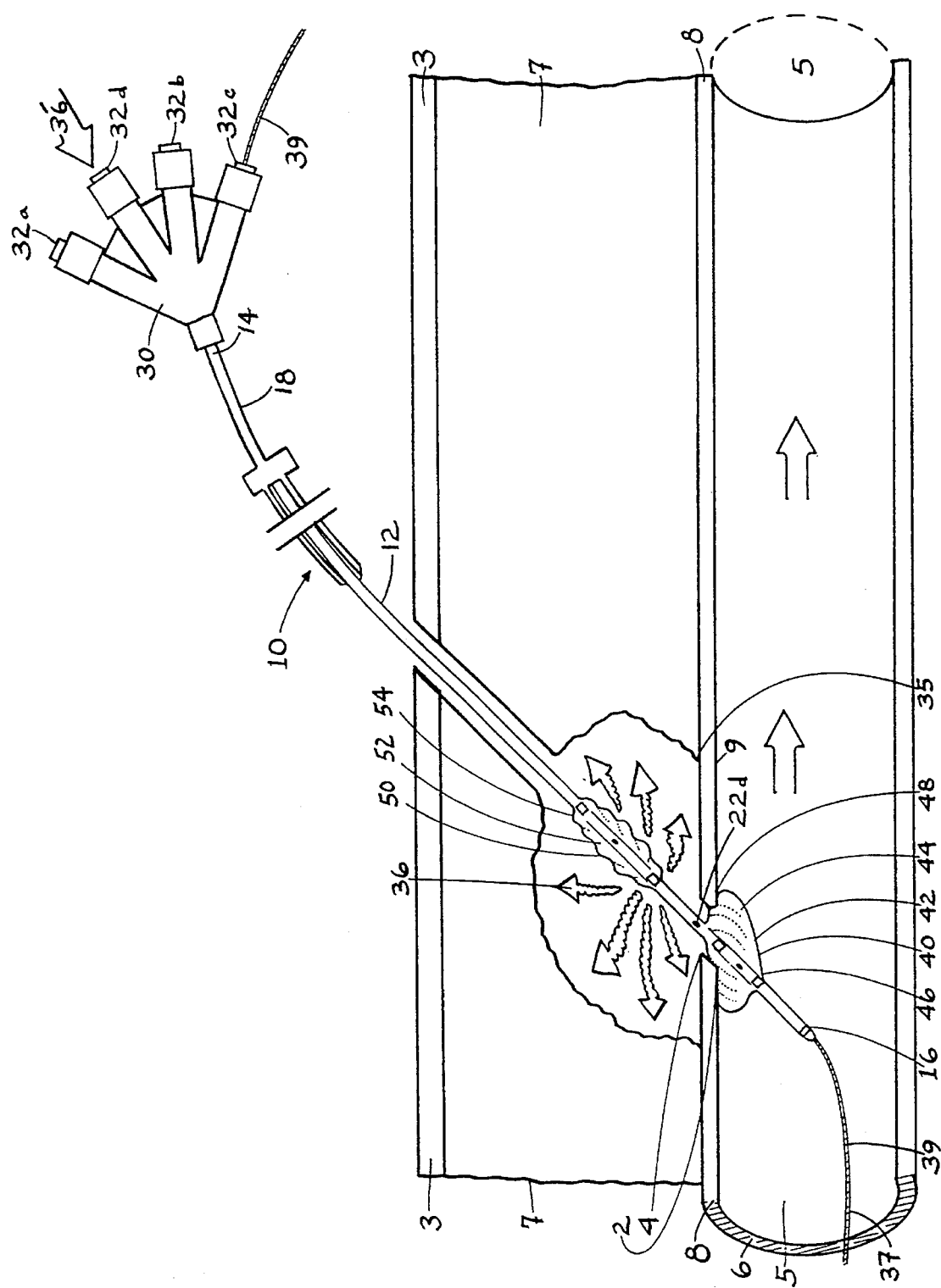
FIG. 4 shows with the apparatus depicted in FIGS. 1–3 with continued first balloon closure of the arteriotomy site while injecting patient specific sealant through the lumen of the first catheter shaft into the cavity created by debriding the anterior wall.
Figure 5A:
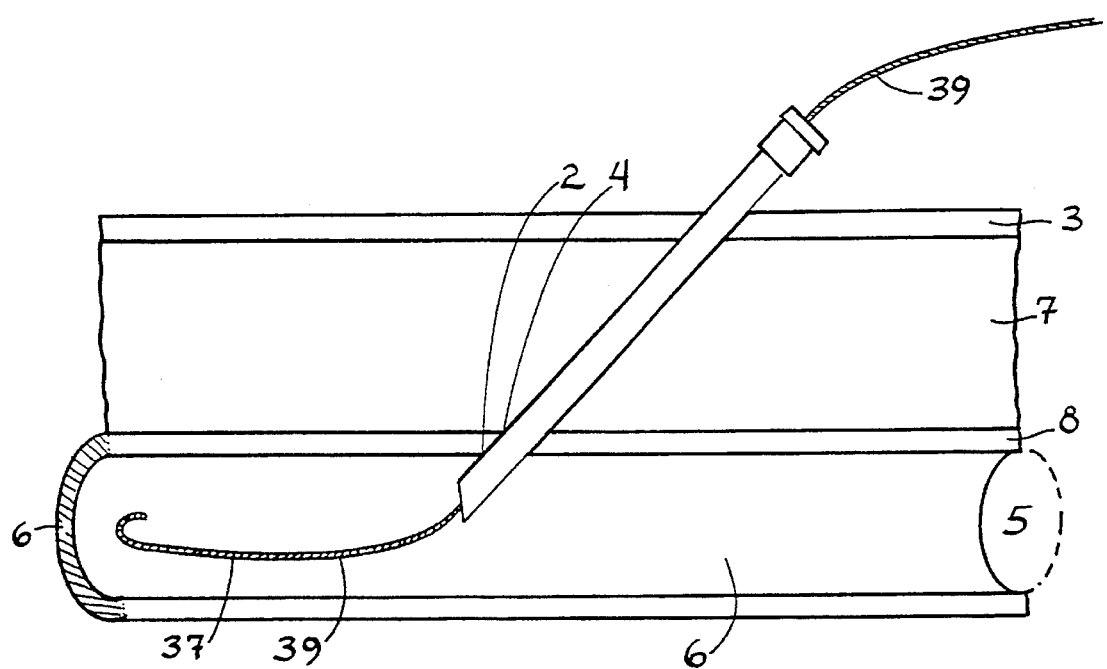
FIG. 5A–D are longitudinal cross sections that show an alternative embodiment of the apparatus featuring a single catheter and balloon for occluding the intravascular opening of the arteriotomy and a means for delivery of a semi-solid plug of sealant material inserted over the catheter.
Figure 5B:
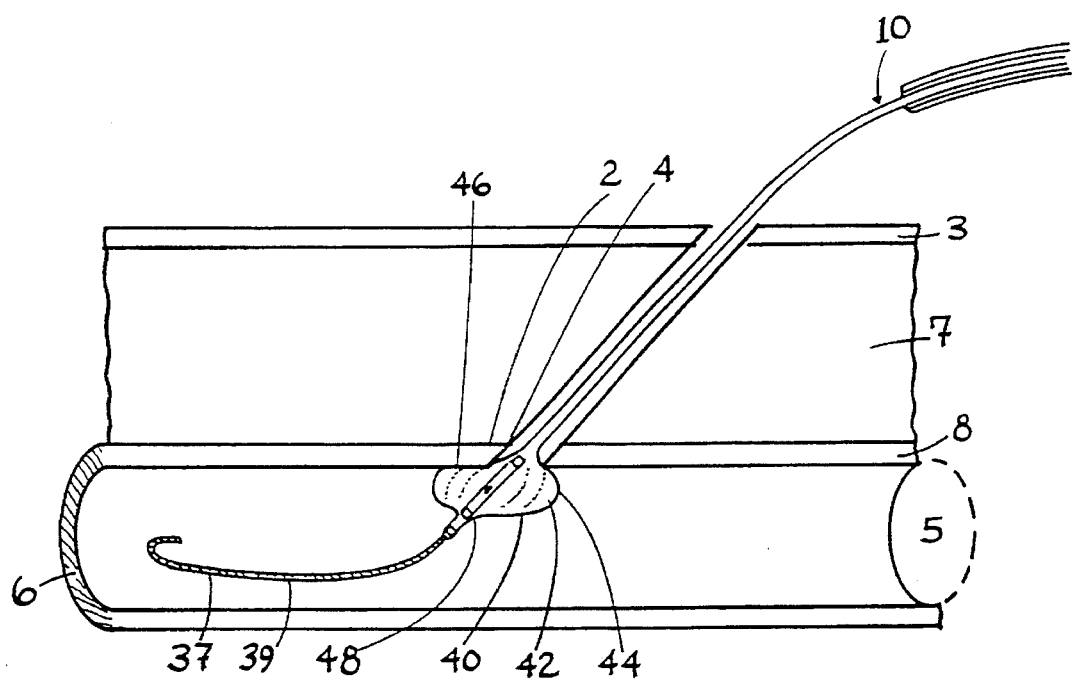
Figure 5C:
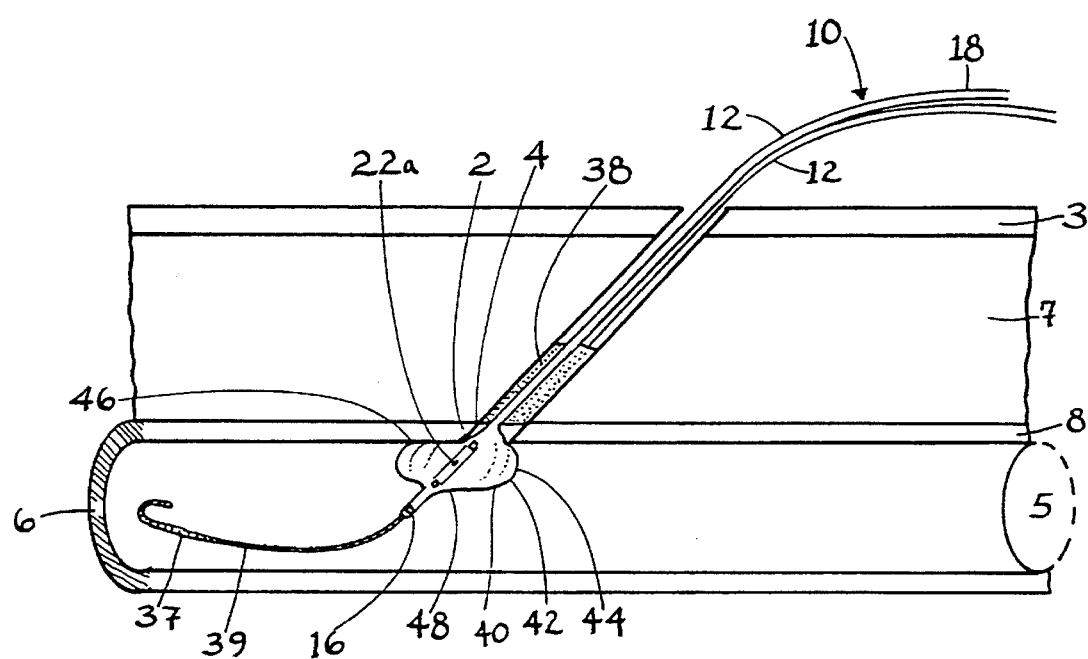
Figure 5D:
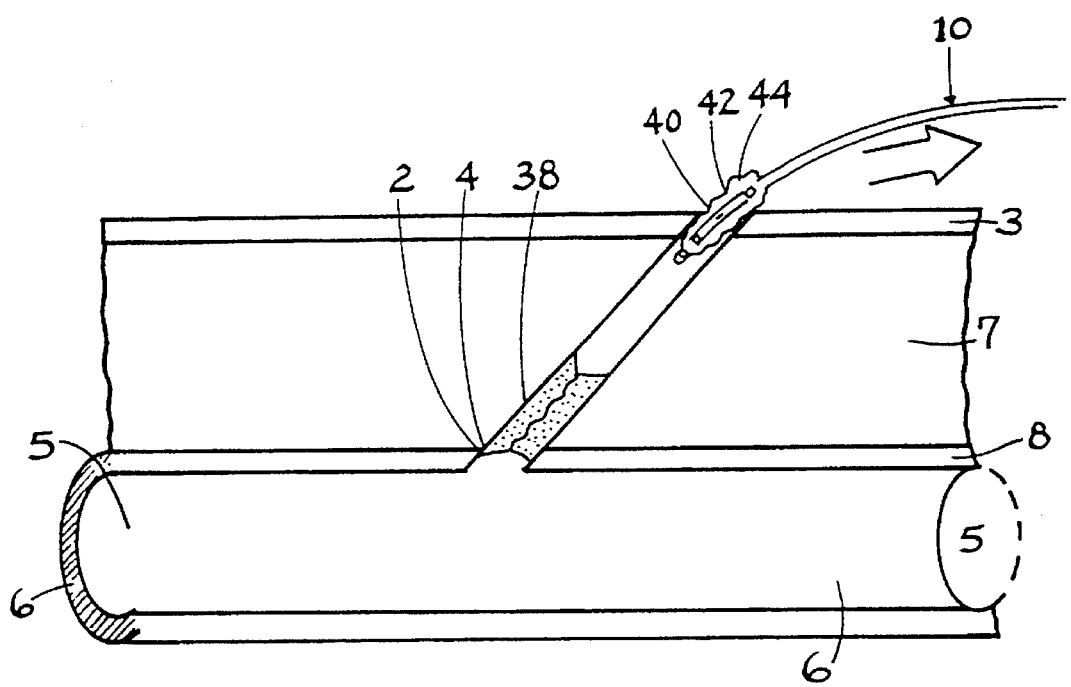

In the embodiment depicted in FIGS. 1–4, the closed volume of the first balloon 44 is in fluid communication with a first lumen 26a of the first catheter 12 and a first balloon port 32a on the collar 30. The first balloon 44 may be inflated or deflated by a fluid added or removed respectively through the first balloon port 32a and the first lumen 26a of the first catheter 12. As shown in FIGS. 2–4, the first balloon 44 can be wedge shaped, having a narrower nose end 46 located proximally on the first catheter 12 and a wider tail end 48 located distally on the catheter 12. When the first balloon 44 is inflated, the nose end 46 is capable of plugging and temporarily occluding the intravascular opening 4 of the arteriotomy site 2.

As shown in FIGS. 1–4, the apparatus 10 for sealing an arteriotomy site 2 may additionally comprise a means 50 for debriding subcutaneous tissue 7 from the exterior surface 9 of the anterior arterial wall 8 proximate to the arteriotomy site 2. The debriding means 50 can comprise an extravascular expandable member 52 on the external surface 18 of the first catheter 12 adjacent the distal end 16 thereof and located at a first predetermined distance therefrom. The first predetermined distance, as used herein, means at least the distance measured from the tip of the nose end 46 of the first balloon 44 of a properly positioned first catheter 12, as shown in FIG. 2, to the exterior surface 9 of the anterior arterial wall 8. As can be appreciated, this distance can vary depending upon the size and thickness of the subject artery and can vary according to the choice of the debriding means 50. The first catheter 12 can be designed to have appropriate distances between the intravascular and extravascular expandable members that are selected over a range of vessel sizes and wall thicknesses. Vessel wall thicknesses vary with age and can be determined utilizing methods known in the art such as ultrasound or other imaging techniques. The femoral artery, for example, typically has a vessel wall thickness of approximately 1 mm. The first predetermined distance of the embodiment shown in FIG. 2 for use in femoral arteriotomy closure with a wall thickness of 1.0 mm therefore, would be at least 1.1 mm from the nose end 46 of the first balloon 44.

As depicted in FIGS. 1–4, the extravascular expandable member 52 can be a second balloon 54 surrounding a portion of the first catheter 12. The second balloon 54, which is a closed volume, overlays a second opening 22b on the external surface 18 of the first catheter 12 wherein the closed volume of the second balloon 54 is in fluid communication with a second lumen 26b of the first catheter 12 and second balloon port 32b on the collar 30. The second balloon 54 may be inflated or deflated by a fluid added or removed respectively through the second balloon port 32b and the second lumen 26b of the first catheter 12. Inflation of the second balloon 54 debrides the subcutaneous tissue 7 from the external surface 9 of the anterior arterial wall creating a cavity 35 over the arteriotomy site 2 for depositing sealant material 36.

Alternatively, the second balloon 54, shown in FIG. 3, can be cup shaped (resembling the type shown in FIG. 8) having a dorsal surface 58 aligned with the proximal end 14 of the first catheter 12 and ventral surface 60 aligned with the distal end 16 of the first catheter 12. Inflation of the second balloon 54 causes the dorsal surface 58 to debride subcutaneous tissue 7 from the exterior surface 9 of the anterior arterial wall 8 and the ventral surface 60 to form a sub-balloon chamber (similar to the sub-balloon chamber 61 shown in FIG. 8) with the debrided exterior surface 9 of the anterior arterial wall 8 proximate to the arteriotomy site 2.

FIG. 4 shows one embodiment of a means for delivering a material 36 which is capable of forming a substantially fluid tight seal to the arteriotomy site 2. The delivering means can comprise a fourth opening 22d of the first catheter 12 located adjacent the distal end 16 thereof at a second predetermined distance therefrom in which the fourth opening 22d is in fluid communication with a fourth lumen 26d (shown in FIG 1B of the first catheter 12 and with a sealant port 32d on the collar 30. A liquid sealant 36 can be delivered into the cavity 35 at the arteriotomy site 2. The second predetermined distance, as used herein, refers to at least the distance measured from the tip of the nose end 46 of the first balloon 44 of a properly positioned first catheter 12, as shown in FIGS. 2–4 to a point external of the exterior surface 9 of the anterior arterial wall 8. As can be appreciated, this distance can vary depending upon the size and thickness of the subject artery. The first catheter 12 can be designed to have appropriate distances between the occluding means 40 and the fourth opening 22d of the delivery means such that a properly positioned first catheter 12 can deliver sealant material 36 to the proper location of the extravascular space adjacent the arteriotomy site 2 over a range of vessel sizes and thicknesses.

An alternative embodiment is shown in FIG. 5 to the above delivery means. The delivering means depicted in FIG. 5 comprises a preformed semi-solid or solid plug 38 of the sealant material 36 slidably positioned around the external surface 18 of the first catheter 12 and a means for sliding the plug (not shown) of the sealant material 36 distally along the longitudinal axis of the first catheter 12. This sliding plug 38 of sealant material 36 creates a sealing engagement with the extravascular opening of the arteriotomy site 2. The subcutaneous tissue 7 acts to hold the plug 38 in proper position.

As shown in FIGS. 1–4, the apparatus 10 for sealing an arteriotomy site 2 can further comprise a means 37 for guiding the first catheter 12 into proper position in the arteriotomy site 2. The guiding means 37 can comprise a guidewire 39 slidably disposed through and removable from a lumen 26c which has third opening 22c at the distal end 16 of the first catheter 12 and a guidewire port 32c on the collar 30.

The apparatus 10 depicted in FIGS. 1–4 can also further comprise a hollow elongated sheath 63 (of the type shown in FIGS. 6–9) having a first end 65, a second end 67, an external surface 69, an internal surface 68 defining an internal volume 66 which is capable of slidably receiving the apparatus 10 therein. The sheath 63 protects the apparatus 10 during positioning within the arteriotomy site 2. The sheath 63 can then be slidably retracted proximally out of the arteriotomy site 2 along the longitudinal axis of the first catheter 12.

Referring now to FIGS. 6–9, a presently preferred embodiment of the arteriotomy closure apparatus 10 is shown. The apparatus 10, as shown, comprises a first elongated flexible catheter 12 that has a means 40 for temporarily occluding the intravascular opening 4 of the arteriotomy site 2, and a means for delivering a material to the arteriotomy site 2 that is capable of forming a substantially fluid tight seal of the arteriotomy site 2. The debriding means 50 for debriding subcutaneous tissue 7 is located on a second elongated flexible catheter 72.

The first flexible catheter 12, shown in FIGS. 6–9 has a proximal end 14, a distal end 16, an external surface 18, and a wall portion 28 defining at least one lumen 26a–d, which extends substantially the entire length of the first catheter 12, and at least one opening 22a–d through the external surface 18 of the catheter 12 which is located adjacent to the distal end 16. The proximal end 14 of the lumen 26a–d is in fluid communication with the external surface 18 of the first catheter 12 via the opening 22.

The first catheter 12 may further comprises a collar 30 having at least one port 32a–d. The port 32 is connected to the lumen (or lumens) 26 of the first catheter 12 at its proximal end 14 such that the port (or ports) 32a–d are in fluid communication witch the lumen 26 of the first catheter 12.

Figure 6A:
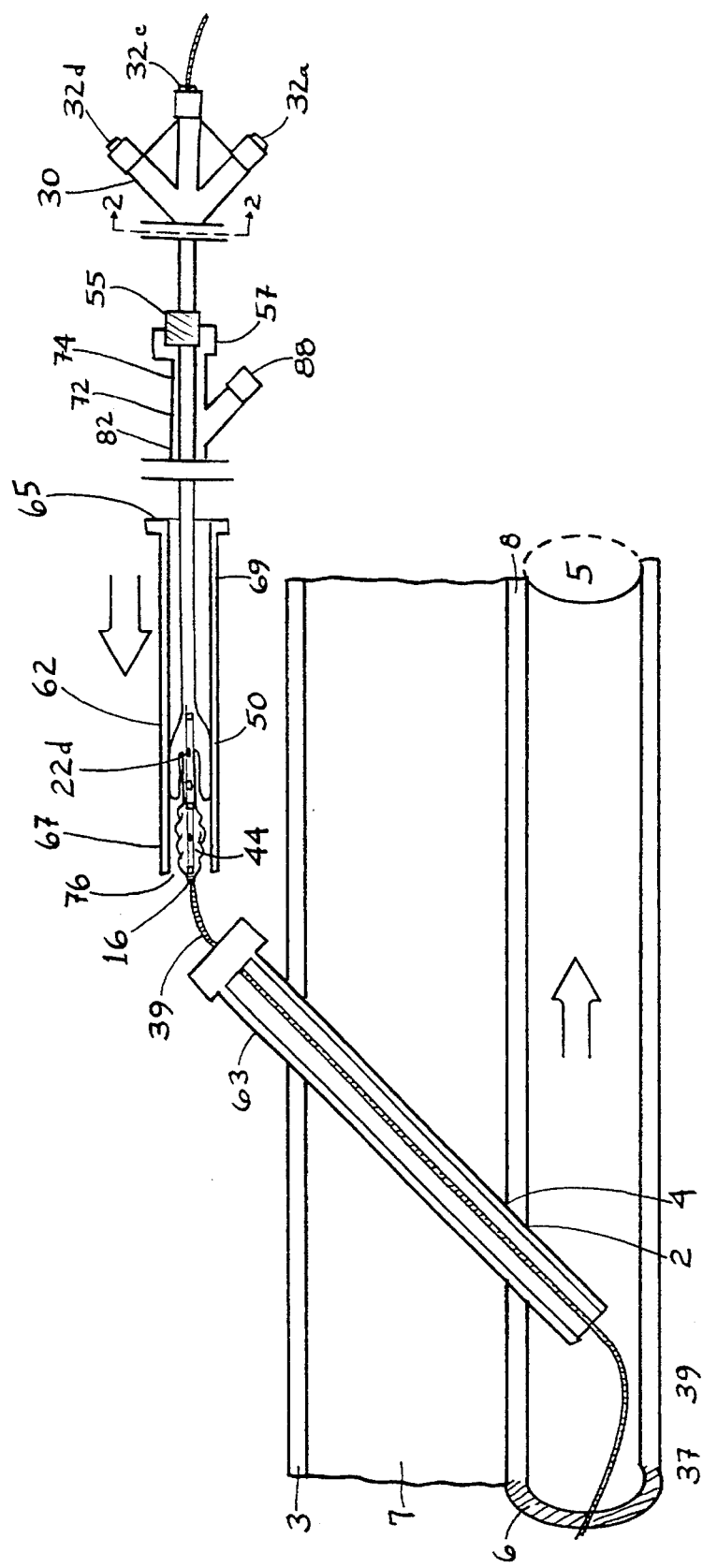
FIG. 6A is a longitudinal cross section of one embodiment that shows the apparatus having first and second interlocking catheters enclosed within a protective sheath as it is being threaded over the guidewire into proper position in the arteriotomy site.
Figure 6B:
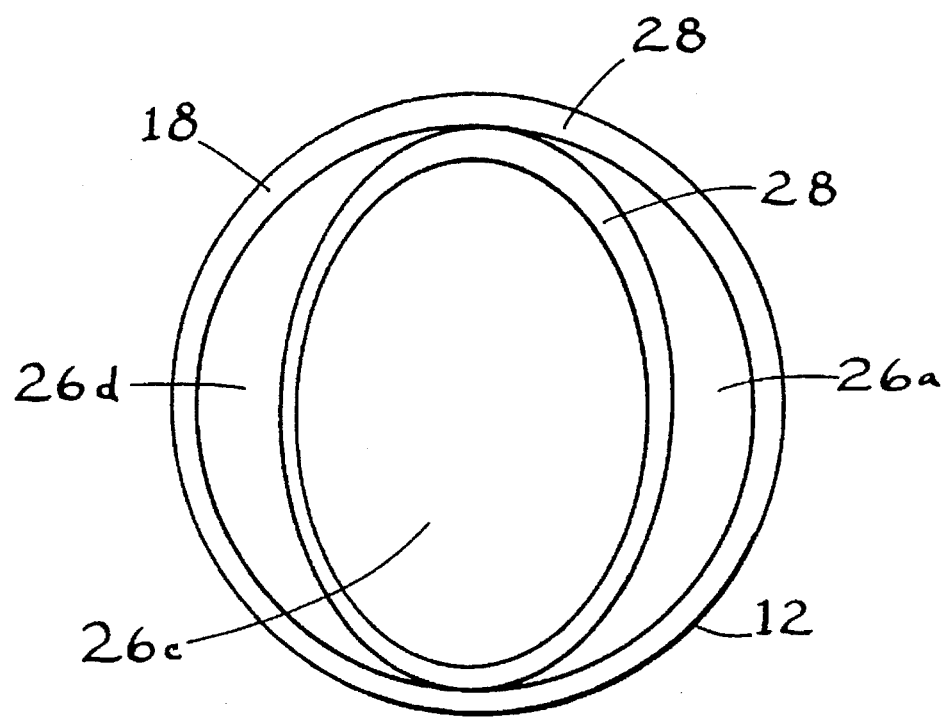
FIG. 6B is a cross-sectional view of the catheter shown in FIG. 6A taken along lines 2—2.
Figure 7:
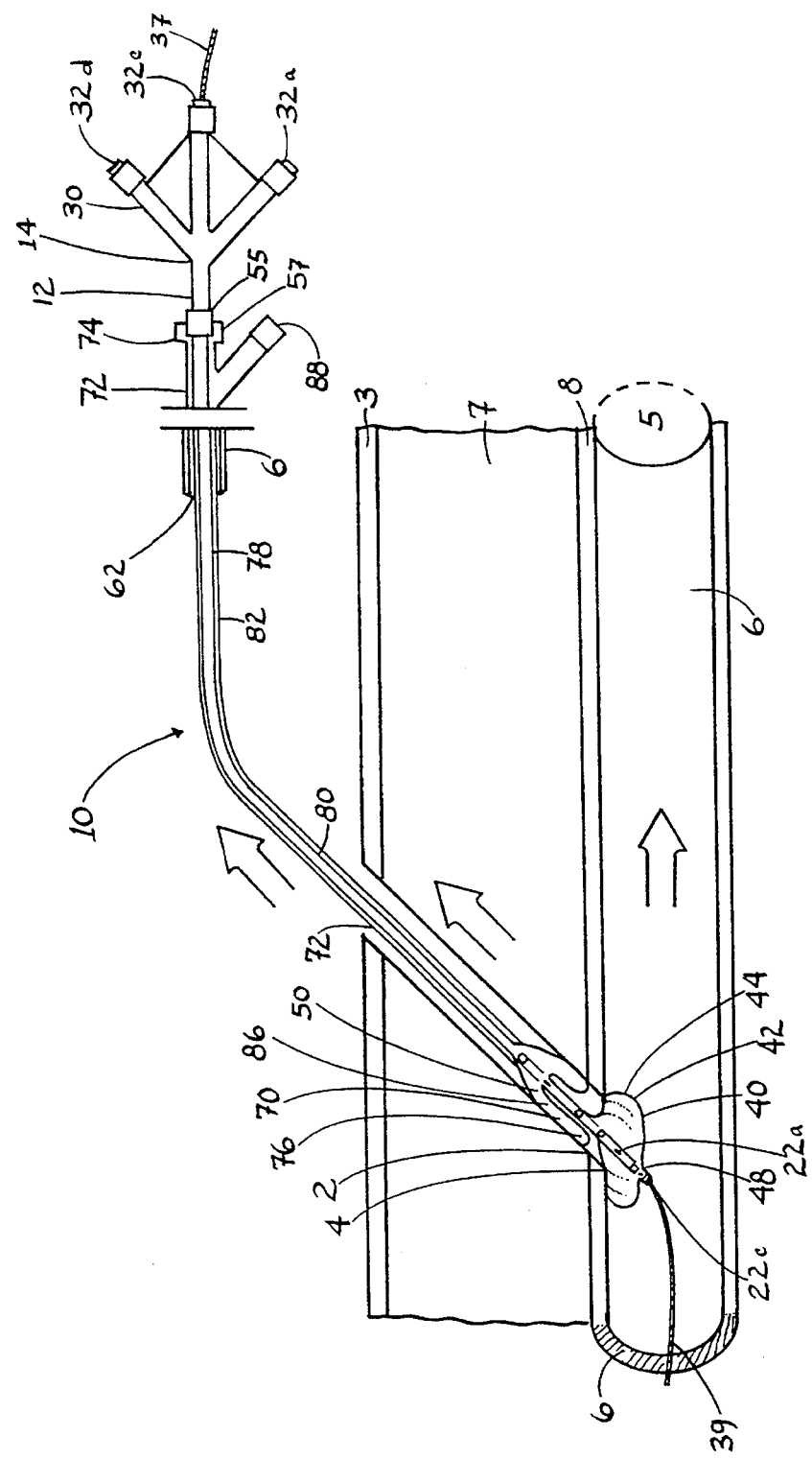
FIG. 7 shows the embodiment of FIG. 6 with complete withdrawal of the sheath, inflation of the first balloon and a partial withdrawal of the interlocked first and second catheters until the first balloon is snugly in position so as to occlude the opening in the internal arterial wall of the arteriotomy.
Figure 8:
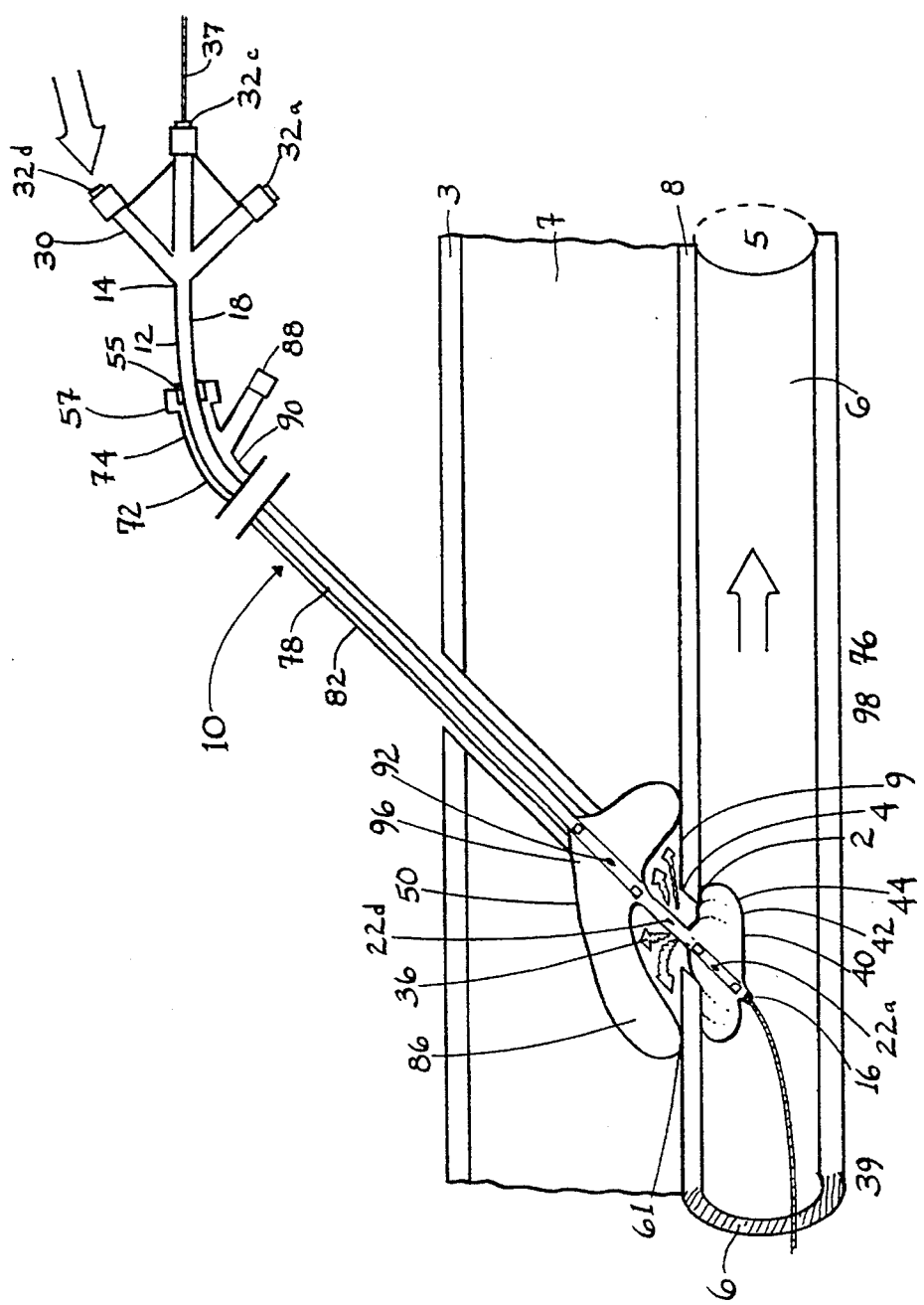
FIG. 8 shows the embodiment depicted in FIGS. 6–7 with inflation of a second balloon located on the second catheter thereby debriding the subcutaneous tissue and forming a sub-balloon chamber over the extra-vascular opening of the arteriotomy. The sub-balloon chamber formed by the inflation of second balloon is utilized to confine a liquid sealant material injected through an opening in the first catheter.
Figure 9:
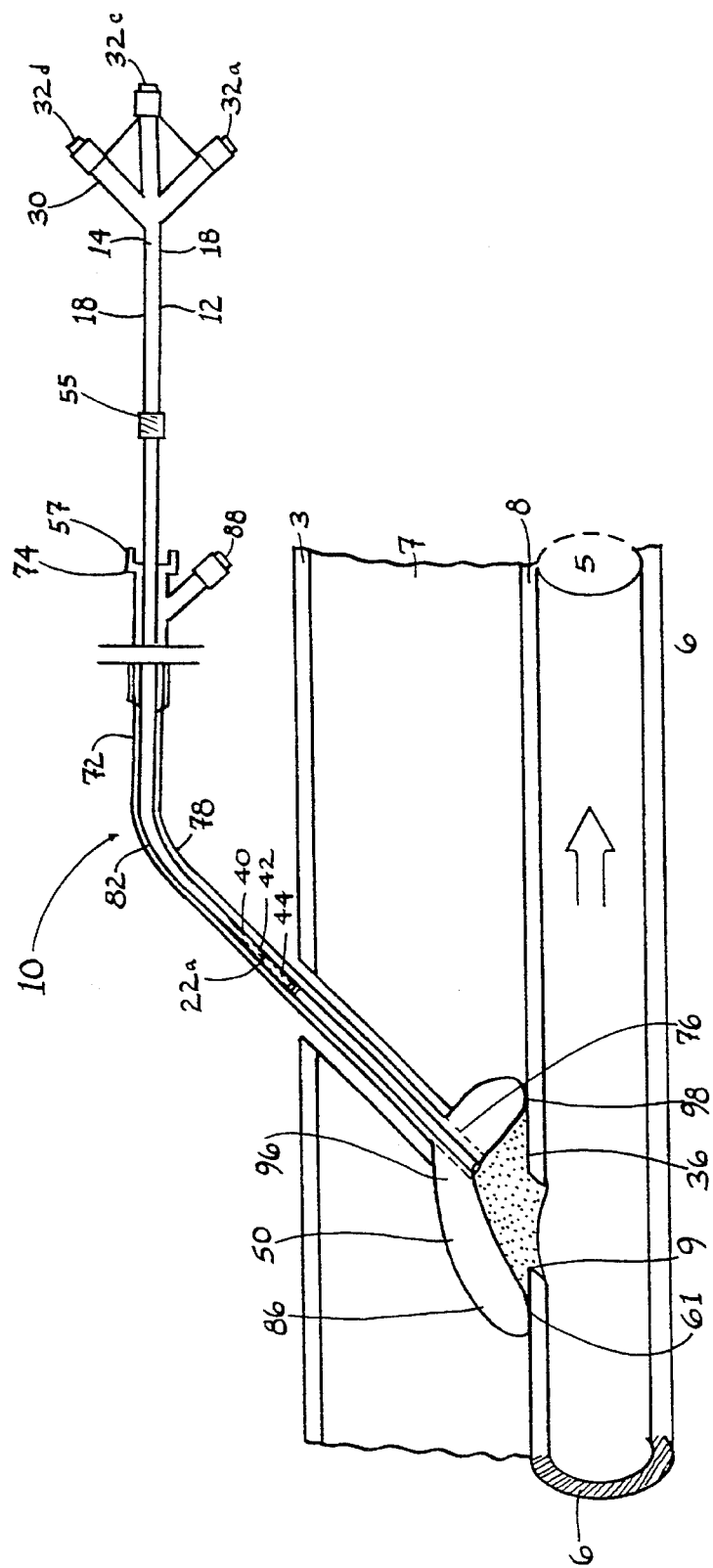
FIG. 9 shows the embodiment of FIGS. 6–8 and after deflating the first balloon withdrawal of the guidewire and the first catheter from the arteriotomy site. The solidifying sealant material is held in position by the inflated second balloon.
Figure 10A:
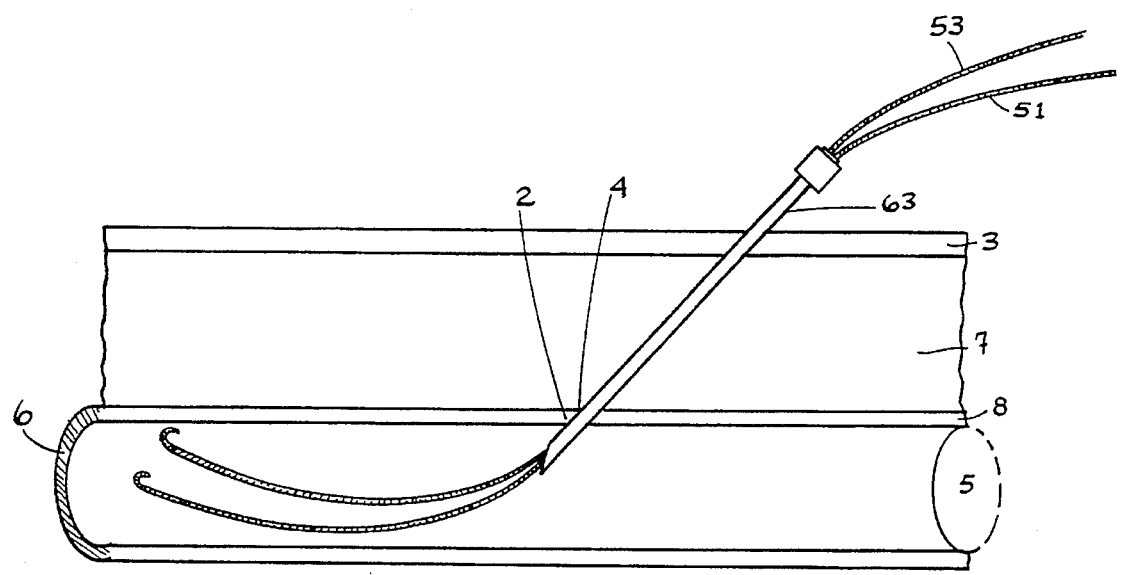
FIG. 10A–D) are longitudinal cross sections that show another embodiment of the apparatus featuring two guidewires and the two catheters.
Figure 10B:
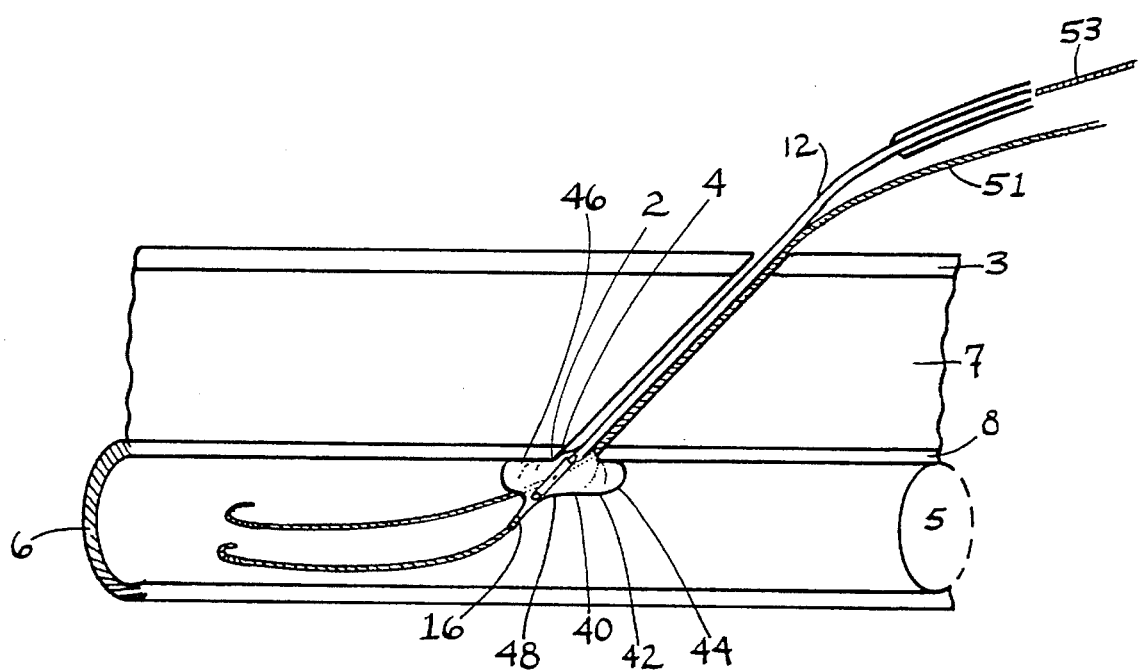
Figure 10C:
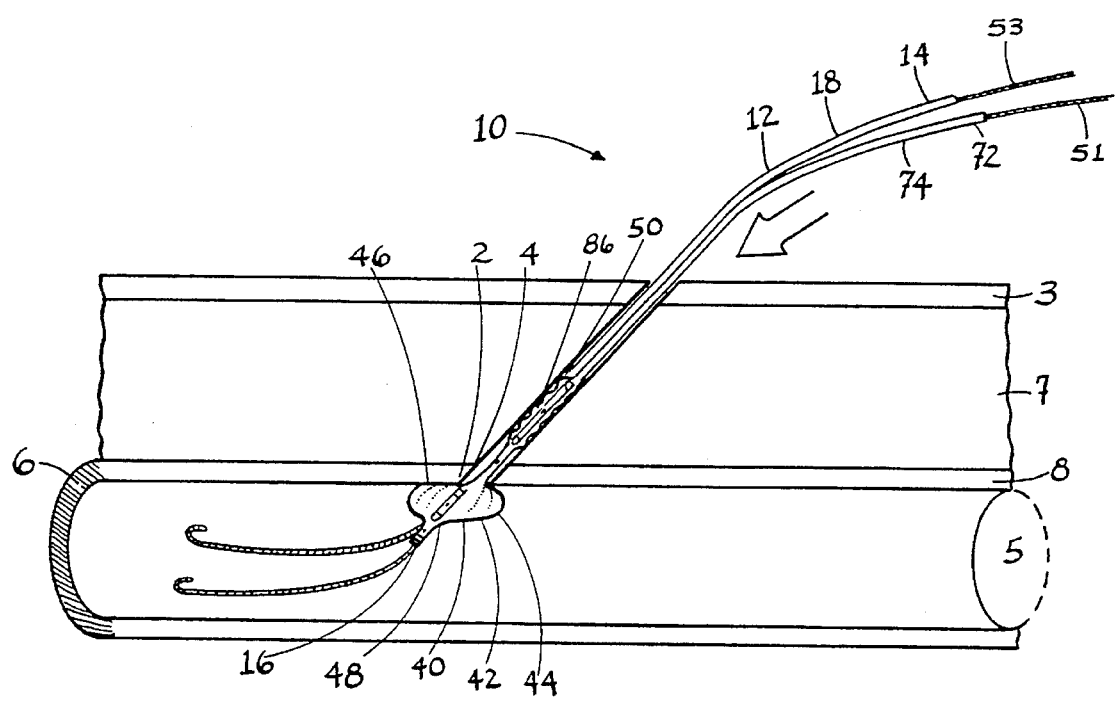
Figure 10D:
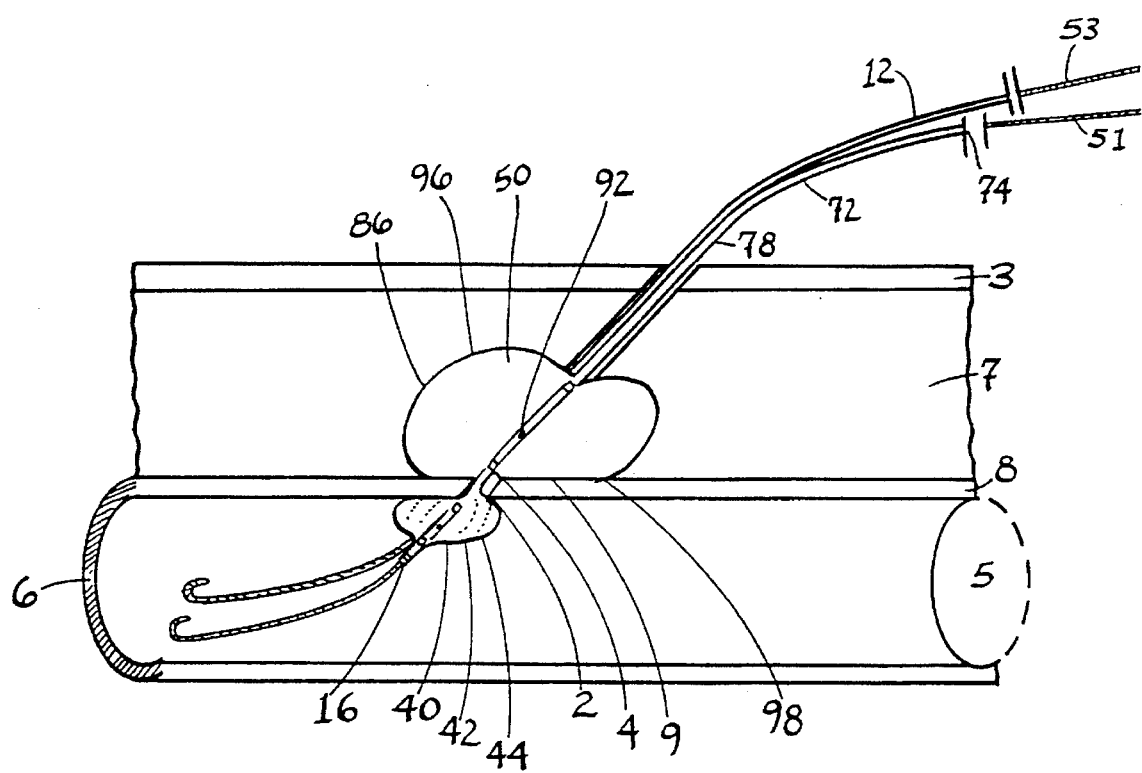

Still referring to FIGS. 6–9, the means 40 for temporarily occluding the intravascular opening 4 of the arteriotomy site 2 can be located adjacent to the distal end 16 of the first catheter 12. The occluding means 40 can be positioned in the intravascular space of the patient's artery 6 proximate to the arteriotomy site 2, as shown in FIG. 7 and FIG. 8. The occluding means 40 may comprise an intravascular expandable member 42 on the external surface 18 of the first catheter 12. The intravascular expandable member 42 of the presently preferred embodiment is a first balloon 44, which is a closed volume, surrounding a portion of the external surface 18 of the first catheter 12. The first balloon 44 overlays a first opening 22a in the external surface 18 of the first catheter 12 and a first balloon port 32a on the collar 30. The closed volume of the first balloon 44 is in fluid communication with a first lumen 26a of the first catheter 12 and a first balloon port 32a on the collar 30. The first balloon 44 may be inflated or deflated by a fluid added or removed respectively through the first balloon port 32a and the first lumen 26a of the first catheter 12. As shown in FIGS. 7–9, the first balloon 44 can be wedge shaped having a narrower nose end 46 located proximally on the first catheter 12 and a wider tail end 48 located distally on the catheter 12. When the first balloon 44 is inflated, the nose end 46 is capable of plugging and temporarily occluding the intravascular opening 4 of the arteriotomy site 2.

As shown in FIGS. 6–9, the debriding means 50 can comprise an extravascular expandable member 70 positioned on a second elongated flexible that the first catheter 12 may be inserted into the central bore 82 of the second catheter 72 and removably interlocked thereto via the interlocking members 55 and 57.

FIG. 8 shows the means for delivering a material 36 which is capable of forming a substantially fluid tight seal to the arteriotomy site 2. The delivering means comprises a fourth opening 22d of the first catheter 12 and with a sealant port 32d on the collar 30 located adjacent the distal end 16 thereof at a second predetermined distance therefrom. The fourth opening 22d is in fluid communication with a fourth lumen 26d (shown in FIG. 6B) of the first catheter 12 such that a liquid sealant 36 can be delivered to the arteriotomy site 2.

As shown in FIGS. 6–9, the apparatus 10 for sealing an arteriotomy site 2 can further comprise a means 37 for guiding the first catheter 12 into proper position in the arteriotomy site 2. The guiding means 37 can comprise a guidewire 39 slidably disposed through and removable from one lumen 26c which has a third opening 27c at the distal end 16 of the first catheter 12 and a guidewire port 32c on the collar 30.

In the alternative configuration shown in FIG. 10, the guiding means 37 comprises a first guidewire 53 slidable disposed through and removable from a third lumen 26c of the first catheter 12 and a second guidewire 51 slidable disposed through and removable from the central bore 82 of the second catheter 72.

In FIGS. 6–9, the apparatus 10 for sealing an arteriotomy site 2 can also comprise a hollow elongated sheath 63 having a first end 65, a second end 67, an external surface 69, an internal surface 68 defining an internal volume 66 which is capable of slidable receiving the apparatus 10 therein. The sheath 63 catheter 72 having a front end 74, a rear end 76, an outer surface 78, and a body portion 80. The debriding means 50 can be located adjacent to the rear end 76. The second catheter 72 of the presently preferred embodiment comprises a central bore 82 and a means for expanding the extravascular expandable member 70. The central bore 82 is defined by the body portion 80 which extends through the length of the second catheter 72, allowing the front end 74 to communicate with the rear end 76. In the presently preferred embodiment, extravascular expandable member 70 is a second balloon 86, having a closed volume, surrounding a portion of the outer surface 78 of the second catheter 72. The expanding means comprises an inflation port 88 located adjacent to the front end 74 of the second catheter 72. The inflation port 88 is in fluid communication with the second balloon 86 via an inflation lumen 90 extending through the body portion 80 and terminating at an opening 92 in the outer surface 78 of the second catheter 72 inside the closed volume of the second balloon 86. The second balloon 86 can be inflated or deflated by a fluid added or removed respectively through the inflation port 88. The second balloon 86 can be cup shaped, having a dorsal surface 96 aligned with the front end 74 of the second catheter 72 and ventral surface 98 aligned with the rear end 76 of the second catheter 72. As shown in FIG. 8, inflation of the second balloon 86 causes the dorsal surface 96 to debride subcutaneous tissue 7 from the exterior surface of the anterior arterial wall 8 and the ventral surface 98 to form a sub-balloon chamber 61 with the debrided exterior surface 9 of the anterior arterial wall 8 proximate to the arteriotomy site 2.

As shown in FIGS. 6–9, the central bore 82 of the second catheter 72 can be sized complimentary to the first catheter 12 such that at least a portion of the first catheter 12 can be slidably and removably inserted into and pass through the central bore 82. The first catheter 12 can have an interlocking member 55 located on the external surface 18 of the wall portion 28 adjacent the proximal end 16 thereof. The second catheter 72 can have a complimentary interlocking member 57 located on the outer surface 78 of the front end 74 such protects the apparatus 10 during positioning within the arteriotomy site 2 such that the sheath 63 can then be slidable retracted proximally out of the arteriotomy site along the longitudinal axis of the second catheter 12.

The lumens 26a–d for the apparatus 10 shown in FIG 1B and FIG 6B may be of different types. One variation of lumens 26 in the first catheter 12 consists to a plurality of channels which are non-overlapping, independent, side-by-side passages. Another variation produces a plurality of channels utilizing concentric, overlapping passages. Depending upon the configuration of the apparatus and the choice of delivery, debriding, expanding, and occluding means, the number of independent lumens can vary between at least one to four or more.

The present invention also provides methods of sealing an arteriotomy site in a patient against the internal to external pressure gradient produced by the patient's cardiovascular system. In particular, one method of the present invention comprises the steps of:

a. placing into proper position within the arteriotomy site an apparatus having a means for temporarily occluding the intravascular opening of the arteriotomy site when said occluding means is positioned in the intravascular space of the patient's artery proximate to the arteriotomy site and having a means for delivering a material to the arteriotomy site that is capable of forming a substantially fluid tight seal of the arteriotomy site;

b. occluding temporarily the intravascular opening of the arteriotomy site with said occluding means;

c. delivering a material to the arteriotomy site via said delivery means which is capable of forming a substantially fluid tight seal of the arteriotomy site; and d. withdrawing said apparatus from the arteriotomy site.

The method can further comprise prior to delivering the sealant to the arteriotomy site, they step of debriding subcutaneous tissue from the exterior surface of the anterior arterial wall proximate to the arteriotomy site. One skilled in the art can appreciate that the choice of sealant material will dictate whether debriding the anterior arterial wall is necessary. For example, when a solid or semi-solid plug of patient specific sealant material is used, it is preferable not to debride the anterior arterial wall.

This method can also comprise preparing a patient specific sealant material comprised of components from the patients' own blood prior to the arteriotomy procedure. An example of a patient specific sealant is autologous fibrin glue which can be prepared by methods known in the art and described in, e.g., *Blood Review* (1991)5:240–244; *Eur. J. Cardio-Thorac. Surg.*, (1992) 6:52–54; and *J. Neurosurg.*, 76:626–628 (1992)

The present invention also provides a method of sealing an arteriotomy site in a patient against the internal to external pressure gradient produced by the patient's cardiovascular system such that said method is capable of being performed by a single operator, comprising the steps of:

a. placing into proper position within the arteriotomy site an apparatus comprised of i) a first catheter having a means for temporarily occluding the intravascular opening of the arteriotomy site when said occluding means is positioned in the intravascular space of the patient's artery proximate to the arteriotomy site and having a means for delivering a material to the arteriotomy site that is capable of forming a substantially fluid tight seal of the arteriotomy site, and ii) a means for debriding subcutaneous tissue from the exterior surface of the anterior arterial wall proximate to the arteriotomy site;

b. occluding temporarily the intravascular opening of the arteriotomy site with said occluding means;

c. debriding the exterior surface of the anterior arterial wall proximate to the arteriotomy site with said debriding means;

d. delivering a material to the arteriotomy site via said delivery means which is capable of forming a substantially fluid tight seal of the arteriotomy site; and e. withdrawing said apparatus from the arteriotomy site.

The arteriotomy opening (arteriotomy site 2) as shown in the figures can be created by, e.g., the Seldinger technique, which briefly entails inserting a needle (not shown) through the skin 3, subcutaneous tissue 7, anterior arterial wall 8 and into the arterial lumen 5. A guidewire 39 is inserted through the needle and into the arterial lumen 5. After inserting the guidewire 39, the skin 3 and subcutaneous tissues 7 are compressed against the anterior arterial wall 8 with sufficient force to impede blood flow. This sufficiently reduces intraluminal pressure to prevent seepage of blood through the arteriotomy site 2. A tubular device (not shown) typical in the industry which consists of an inner and removable stiff tube introducer with a tapered end (not shown) and a separate sheath 62 is inserted into the arteriotomy opening. The tubular apparatus is threaded over the guidewire 39 and inserted through the subcutaneous tissue 7 into the arterial lumen 5. After this, the inner introducer member (not shown) and guidewire 39 are removed, leaving the sheath 62 in the arterial lumen 5. After performing any of a number of procedures utilizing the arteriotomy opening, the surgeon must then seal the opening of the arteriotomy site 2.

The presently preferred method of the invention for closure of the arteriotomy site 2 utilizes the apparatus shown in FIGS. 6–9. In particular, the method may involve inserting another, narrower diameter guidewire 39 through the sheath 63 and into the arterial lumen 5. The method then requires placing the apparatus 10 into proper position within the arteriotomy site 2. As shown in FIG. 6, the apparatus 10 can be comprised of a tear away sheath 62, a first catheter 12, and a second catheter 72, and can be introduced into the arteriotomy site over the guidewire 39. However, the method may be performed by introducing the apparatus 10 directly into the arteriotomy without a guidewire 39. The apparatus 10 has a means 40 for temporarily occluding the intravascular opening 4 of the arteriotomy site 2, a means for debriding subcutaneous tissue 7 from the exterior surface 9 of the anterior arterial wall 8 proximate to the arteriotomy site 2, and a means for delivering a material 36 to the arteriotomy site 2 that is capable of forming a substantially fluid tight seal of the arteriotomy site 2. Manual external compression of the vascular lumen is applied proximal to the arteriotomy site 2 during positioning of the apparatus 10 to impede blood flow and to reduce intraluminal pressure and thus prevent seepage of blood through the arteriotomy site 2.

Once the apparatus 10 is in position, the method next involves placing the occluding means 40 of the apparatus 10 within the intravascular space of the patient's artery 6 proximate to the arteriotomy site 2. Simultaneously, the method involves withdrawing the sheath 63 and tear away sheath 62 to a position external to the skin 3 and while leaving the interlocked first catheter 12, and second catheter 72 in an unchanged position.

The method next involves occluding temporarily the intravascular opening 4 of the arteriotomy site 2. This is accomplished by releasing the external compression of the arterial lumen 5 while the first balloon 44 of the first catheter 12 is inflated, and the interlocked first catheter 12 and second catheter 72 are withdrawn over the guidewire 39 into a position so as to occlude the intravascular opening 4 at the arteriotomy site 2.

Then, the method entails debriding subcutaneous tissue 7 from the exterior surface 9 of the anterior arterial wall 8 proximate to the arteriotomy site 2. This is accomplished by partially inflating the second balloon 86 of the second catheter 72 to displace subcutaneous tissue 7 in the extravascular space directly overlying the anterior arterial wall 8 adjacent to the arteriotomy site 2. As the aforementioned occurs, second balloon 86 inflation initiates the creation of the sub-balloon chamber 61. The walls of the sub-balloon chamber 61 are formed by ventral surface 98 of the second balloon 86, and by the debrided anterior arterial wall 8 and closed arteriotomy site 2 adjacent to rear end 76 at the second catheter 72. Debriding subcutaneous tissue also disrupts tissue planes and cells sufficient to release tissue factors, promoting conditions favorable to coagulation. Precise location of the second balloon 86 in relationship to the anterior arterial wall 8, arteriotomy site 2, side holes of component 2, and the inflated first balloon 44 is assured by the interlocking and adjoining first catheter 12 and second catheter 72.

The method then entails delivering a material 36 to the arteriotomy site 2 via the apparatus 10 which is capable of forming a substantially fluid tight seal of the arteriotomy site 2. This is accomplished by continued first balloon 44 closure of the arteriotomy site 2 and continued second balloon 86 inflation to maintain the sub-balloon chamber 61. The sub-balloon chamber 61 confines the material 36, e.g., a patient specific sealant, injected through the fourth lumen 26d of the first catheter 12 and exiting from the fourth lumen 22d of the first catheter 12, into the sub-balloon chamber 61. Specifically, the liquid sealant material 36 is confined anteriorly by the inner portion of the inflated second balloon 86 and posteriorly by the sensitized, debrided, anterior arterial wall 8, and adjacent arteriotomy site 2 which is closed by the inflation of the first balloon 44. The injected liquid sealant material 36 reacts with the factors promoting coagulation, released when the tissue planes and cells were disrupted by inflation of the second balloon 86. The liquid sealant 36, combined with these coagulants, becomes firmly adherent to the walls and orifice of the arteriotomy site 2 and adjacent anterior arterial wall 8. Exposure of this sealant to coagulants results in conversion of the liquid sealant material 36 to a tenacious, gelatinous substance.

After completion of the above steps, the method involves withdrawing the first catheter 12 from the arteriotomy site 2. This is accomplished by continued inflation of the second balloon 86 while the first balloon 44 is deflated. The arterial intraluminal pressure exerted on the arteriotomy site 2 prevents movement of the now gelatinous sealant material 36 from the sub-balloon chamber 61 extravascular space to the arterial lumen 5. Continued inflation of second balloon 86 maintains the sub-balloon chamber 61, such that the arterial pressure cannot produce entry of blood from the vascular lumen 5, through the closed arteriotomy site 2, and into the extravascular sub-balloon chamber 61. When the first balloon 44 starts to deflate, dislodgement and proximal movement of the first catheter 12 results from arterial pressure. The arterial pressure is also exerted on the arteriotomy site 2 and sub-balloon chamber 61, but the pressure is counteracted by the tissue forces created by the compressed subcutaneous tissue 7 and by the second balloon 86 adjacent to the anterior arterial wall 8. These opposing pressures from the arterial lumen 5 and sub-balloon chamber 61 wedges the tenacious gelatinous sealant material 36 into an immoveable position as an adherent "plug". The first catheter 12 and guidewire 39 are then removed through the gelatinous sealant 36 and into the central bore 82 of the second catheter 72. The tract left closes as the gelatinous, tenacious, adherent sealant material 36 fills in the space left by the first catheter 12 and guidewire 39. Inflation of the second balloon 86 is continued until the sealant material 36 solidifies, becomes adherent to, and firmly occludes the arteriotomy site 2. After removal of the first catheter 12 and the sealant material 36 solidifies, the second balloon 86 acts as a solid adherent sealant cap which occludes the arteriotomy site 2.

The methods taught by the present invention can also utilize the embodiments as shown in FIG. 1–4. After the arteriotomy is created and ready for closure, manual external compression of the arterial lumen 5 proximal to the arteriotomy site 2 is applied to prevent bleeding at the arteriotomy site 2 during placement of the apparatus 10.

In particular, the method, utilizing the apparatus depicted in FIG 1–4, involves inserting another, narrower diameter guidewire 39 through the sheath and into the arterial lumen 5. The method next requires placing into proper position within the arteriotomy site 2 the apparatus 10 having a means 40 for temporarily occluding the intravascular opening 4 of the arteriotomy site 2, a means for debriding subcutaneous tissue 7 from the exterior surface 9 of the anterior arterial wall 8 proximate to the arteriotomy site 2, and a means for delivering a material to the arteriotomy site 2 that is capable of forming a substantially fluid tight seal of the arteriotomy site 2. This apparatus 10 is introduced over the guidewire 39. However, the method alternatively may involve inserting the apparatus 10 into the sheath directly without a guidewire 39. The occluding means 40 of the apparatus 10 is positioned in the intravascular space 5 of the patient's artery 6 proximate to the arteriotomy site 2. With the apparatus properly positioned, the method involves occluding temporarily the intravascular opening 4 of the arteriotomy site 2. This is accomplished by continued external compression of the arterial lumen 5 while the first balloon 44 is inflated and withdrawn until it is snugly in position so as to compress the artery 6 at the arteriotomy site 2.

Then, the method entails debriding subcutaneous tissue 7 from the exterior surface 9 of the anterior arterial wall 8 proximate to the arteriotomy site 2. This is accomplished by continued first balloon 44 closure of the arteriotomy site 2 while simultaneously inflating the tandem second balloon 54 sufficient to produce a cavity 35 external to and in juxtaposition to the closed arteriotomy site 2, and such that it disrupts tissue planes and cells sufficient to release tissue factors promoting conditions favorable to coagulation.

The method then entails delivering a material 36 to the arteriotomy site 2 via the apparatus 10 which is capable of forming a substantially fluid tight seal of the arteriotomy site 2. This is accomplished by continued injection of the material 36, e.g., patient specific sealant, causing it to flow through the fourth 26d lumen to the fourth opening 22d in sufficient volume to fill the chamber 35 while keeping continuous first balloon 44 closure of the arteriotomy site 2.

After completion of the above steps, the method involves withdrawing the apparatus 10 from the arteriotomy site 2 while applying continued partial external compression sufficient to reduce intraluminal pressure. this external pressure prevents seepage of blood into the sealant material 36 filled chamber 35 while removing the first catheter 12. After removal of the apparatus 10, continued partial external compression sufficient to control intraluminal pressure is applied thus preventing seepage of blood into the sealant material 36 filled chamber 35 but still providing sufficient intraluminal pressure to hinder sealant material 36 entry into the arterial lumen 5.

It is contemplated by the present invention that the methods and apparatus described herein can be used to seal an opening in any vessel of the body including, but not limited to, arteries, veins, lymphatics, and the like. The components of the apparatus, e.g., catheter, balloons, etc., can be dimensioned and configured to seal openings in vessels of varying sizes over a variety of clinical applications.

Although the present invention has been described with reference to specific details of certain embodiments thereof, it is not intended that such details should be regarded as limitations upon the scope of the invention except as and to the extent that they are included in the accompanying claims.

What is claimed is:

1. An apparatus for sealing an arteriotomy site in a patient comprising:

a. a first elongated flexible catheter having a proximal end, a distal end, an external surface, and a wall portion defining at least one lumen extending substantially the entire length of said first catheter, and at least one opening through the external surface of said first catheter located adjacent the distal end, whereby a proximal end of at least one lumen is in fluid communication with the external surface of said first catheter via said opening;

b. means located adjacent the distal end of said first catheter for temporarily occluding an intravascular opening of the arteriotomy site when said occluding means is positioned in an intravascular space of the patient's artery proximate to the arteriotomy site;

c. a second elongated flexible catheter having a front end, a rear end, an outer surface a body portion, and a central bore defined by the body portion extending through the length of said second catheter communicating the front end with the rear end;

d. means located on said second catheter for debriding subcutaneous tissue from an exterior surface of the anterior arterial wall proximate to the arteriotomy site; and e. means located on a selected one of said catheters for delivering a material to the arteriotomy site that is capable of forming a substantially fluid tight seal of the arteriotomy site.

2. The apparatus of claim 1, wherein said debriding means further comprises an extravascular expandable member located adjacent the rear end of said second catheter, and said second catheter further comprises a means for expanding said extravascular expandable member.

3. The apparatus of claim 2, further comprising a means for guiding said first catheter into proper position in the arteriotomy site.

4. The apparatus of claim 3, wherein said guiding means comprises a first guidewire slidably disposed through and removable from at least one lumen of said first catheter.

5. The apparatus of claim 2, further comprising a hollow elongated sheath having a first end, a second end, an external surface, an internal surface defining an internal volume which is capable of slidably receiving said apparatus therein, wherein said sheath protects said apparatus during positioning within the arteriotomy site whereby said sheath can then be slidably retracted proximally out of the arteriotomy site along the longitudinal axis of said apparatus.

6. The apparatus of claim 2, wherein said first catheter further comprises a collar having a least one port, said port being connected to at least one lumen of said first catheter at its proximal end whereby said port is in fluid communication with that lumen of said first catheter.

7. The apparatus of claim 2, wherein said occluding means comprises an intravascular expandable member on the external surface of said first catheter.

8. The apparatus of claim 7, wherein said intravascular expandable member is a first balloon surrounding a portion of the external surface of said first catheter and having a closed volume, said first balloon overlying a first opening in the external surface of said first catheter wherein the closed volume of said first balloon is in fluid communication with a first lumen of said catheter whereby said first balloon may be inflated or deflated by a fluid added or removed respectively through the first lumen of said first catheter.

9. The first balloon of claim 8, wherein said first balloon is wedge shaped having a narrower nose end located proximally on said catheter and a wider tail end located distally on said first catheter, whereby, when inflated, the nose end is capable of plugging and temporarily occluding the intravascular opening of the arteriotomy site.

10. The apparatus of claim 2, further comprising a means for guiding said second catheter into proper position at the arteriotomy site.

11. The apparatus of claim 2, wherein said extravascular expandable member is a second balloon surrounding a portion of the outer surface of said second catheter, having a closed volume, and said expanding means comprises an inflation port located adjacent the front end of said second catheter which is in fluid communication with said second balloon via an inflation lumen extending through the body portion and terminating at an opening in the outer surface of said second catheter inside the closed volume of said second balloon whereby said second balloon may be inflated or deflated by a fluid added or removed respectively through said inflation port.

12. The second balloon of claim 11, wherein said second balloon is cup shaped having a dorsal surface aligned with the from end of said second catheter and ventral surface aligned with the rear end of said second catheter, whereby inflation of said second balloon causes the dorsal surface to debride subcutaneous tissue from the exterior surface of the anterior arterial wall and the ventral surface to form a sub-balloon chamber with the debrided exterior surface of the anterior arterial wall proximate to the arteriotomy site.

13. The apparatus of claim 2, wherein the central bore of said second catheter is sized complimentary to said first catheter whereby at least a portion of said first catheter can be slidably and removably inserted into and pass through said central bore.

14. The apparatus of claim 13, wherein said first catheter has a male interlocking member located on the external surface of the wall portion adjacent the proximal end thereof and said second catheter has a complimentary interlocking female member located on the outer surface of the front end whereby said first catheter may be inserted into the central bore of said second catheter and removably interlocked thereto via said interlocking members.

15. The apparatus of claim 2, wherein said delivering means comprises a second opening of said first catheter located adjacent the distal end thereof at a predetermined distance therefrom, said second opening being in fluid communication with a second lumen of said first catheter, whereby a liquid sealant can be delivered to the arteriotomy site.

16. The apparatus of claim 2, wherein said material that is capable of forming a substantially fluid tight seal of the arteriotomy site is a patient specific sealant material comprised of components from the patient's blood for sealing the arteriotomy site.

17. The material of claim 16, wherein the patient specific sealant is an autologous fibrin glue.

18. The apparatus of claim 1, wherein said debriding means comprises an extravascular expandable member on the external surface of said first catheter adjacent the distal end thereof and located at a first predetermined distance therefrom.

19. The apparatus of claim 18, wherein said extravascular expandable member is a second balloon surrounding a portion of the external surface of said first catheter and having a closed volume, said second balloon overlying a second opening in the external surface of said first catheter wherein the closed volume of said second balloon is in fluid communication with a second lumen of said first catheter whereby said second balloon may be inflated or deflated by a fluid added or removed respectfully through the second lumen of said first catheter.

20. The second balloon of claim 19, wherein said second balloon is cup shaped having a dorsal surface aligned with the proximal end of said first catheter and ventral surface aligned with the distal end of said first catheter, whereby inflation of said second balloon causes the dorsal surface to debride subcutaneous tissue from the exterior surface of the anterior arterial wall to form a sub-balloon chamber with the debrided exterior surface of the anterior wall proximate to the arteriotomy site.

* * * * *